United States Patent [19]

Kimura et al.

[11] Patent Number: 4,790,869

[45] Date of Patent: Dec. 13, 1988

[54] SULFONAMIDE COMPOUNDS AND SALTS THEREOF, HERBICIDAL COMPOSITIONS CONTAINING THEM

[75] Inventors: Fumio Kimura; Takahiro Haga; Kazuyuki Maeda; Hiroshi Shimoharada; Tsunezo Yoshida; Masahiko Ikeguchi, all of Kusatsu, Japan

[73] Assignee: Ishihara Sangyo Kaisha Ltd., Osaka, Japan

[21] Appl. No.: 9,924

[22] Filed: Feb. 2, 1987

[30] Foreign Application Priority Data

Feb. 7, 1986 [JP] Japan .................................. 61-25246
May 22, 1986 [JP] Japan .................................. 61-118235
Sep. 12, 1986 [JP] Japan .................................. 61-215543

[51] Int. Cl.$^4$ .................. A01N 43/54; C07D 239/47; C07D 417/12
[52] U.S. Cl. ........................................ 71/90; 544/320
[58] Field of Search .................... 71/90; 544/320

[56] References Cited

U.S. PATENT DOCUMENTS 4,604,130 8/1986 Shapiro .................................. 71/90

FOREIGN PATENT DOCUMENTS 0095925 12/1983 European Pat. Off. .
096003 12/1983 European Pat. Off. .
0096003 12/1983 European Pat. Off. .
0142629 5/1985 European Pat. Off. .
59-1480 1/1984 Japan .
60-48988 3/1985 Japan .

OTHER PUBLICATIONS

Patent Abstracts of Japan, vol. 9, No. 180, (C-293) [1903], Jul. 25th, 1985.

Primary Examiner—John M. Ford
Attorney, Agent, or Firm—Oblon, Fisher, Spivak, McClelland & Maier

[57] ABSTRACT

A sulfonamide compound and a salt thereof is represented by the following general formula:

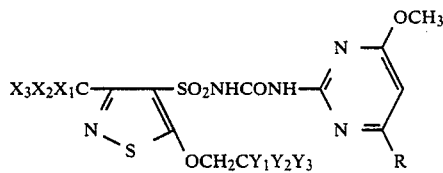

wherein each of $X_1$, $X_2$, and $X_3$ independently represents a hydrogen atom or a halogen atom, each of $Y_1$, $Y_2$, and $Y_3$ independently represents a halogen atom, and R represents a methyl group or a methoxy group, and is effective as an active ingredient of a herbicidal composition.

12 Claims, No Drawings

SULFONAMIDE COMPOUNDS AND SALTS THEREOF, HERBICIDAL COMPOSITIONS CONTAINING THEM

BACKGROUND OF THE INVENTION

1. Field of the Invention

The present invention relates to sulfonamide compounds represented by general formula (I) below and salts thereof, herbicidal compositions containing them as active ingredients, process for producing them, and intermediates thereof.

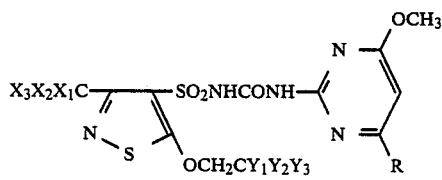

wherein each of $X_1$, $X_2$, and $X_3$ independently represents a hydrogen atom or a halogen atom, each of $Y_1$, $Y_2$, and $Y_3$ independently represents a halogen atom, and R represents a methyl group or a methoxy group.

2. Description of the Prior Art

Isothiazolesulfonamide compounds are known as effective herbicides, as indicated by a general formula in European Patent Application Publication No. 96003. However, sulfonamide compounds of the present invention are not specifically disclosed in this prior patent. This prior patent does not describe applications of sulfonamide compounds as rice plant herbicides, either. Usefulness of isothiazole sulfonamide compounds as herbicides are known by Japanese Unexamined Patent Publication No. 1480/1984 and No. 48988/1985. However, the compounds disclosed in the former prior patent differ from the ones of the present invention in that no substituent group is present at the 5-position of an isothiazole ring. The compounds disclosed in the latter prior patent differ from the ones of the present invention in that the type of substituent group differs from that of the present invention. From these viewpoints, the sulfonamide compounds of the prior art have clearly different chemical structures from those of the present invention.

SUMMARY OF THE INVENTION

The present inventors have made extensive studies on the relation of chemical structures of the above mentioned sulfonamide compounds and physiological activities of these compounds against plants. The present inventors have made further studies for finding an excellent herbicidal effect in a particular sulfonamide compounds which have a methyl group which may be substituted with one or more halogen atoms at the 3-position of an isothiazole ring thereof, which have a 2,2,2-trihalogenoethoxy group at the 5-position thereof, and which have a sulfonylurea chain substituted with a specific pyrimidine group at the 4-position thereof. In particular, the present inventors found that these compounds could selectively kill noxious weeds growing in paddy fields at a low dosage without substantially causing phytotoxicity against rice plants, and thus attained the present invention.

DETAILED DESCRIPTION OF THE PREFERRED EMBODIMENTS

The present invention relates to sulfonamide compounds represented by general formula (I) below and salts thereof, herbicidal compositions containing them as active ingredients, process for producing them, and intermediates thereof.

The sulfonamide compounds of this invention are represented by the following formula (I):

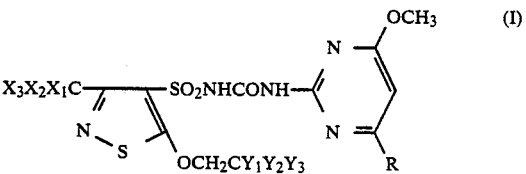

wherein each of $X_1$, $X_2$, and $X_3$ independently represents a hydrogen atom or a halogen atom, each of $Y_1$, $Y_2$, and $Y_3$ independently represents a halogen atom, and R represents a methyl group or a methoxy group.

Examples of the halogen atom represented by $X_1$ to $X_3$ and $Y_1$ to $Y_3$ in general formula (I) are a fluorine atom, a chlorine atom, a bromine atom, and an iodine atom.

In general formula (I), each of $X_1$, $X_2$, and $X_3$ independently represents preferably a hydrogen atom or a fluorine atom, and more preferably a hydrogen atom. Each of $Y_1$, $Y_2$, and $Y_3$ independently represents preferably a chlorine atom or a fluorine atom and, more preferably a fluorine atom. Examples of salts of the sulfonamide compounds are those of alkaline metals such as sodium and potassium, salts of alkaline earth metals such as magnesium and calcium, and salts of substituted or nonsubstituted amines such as methylamine, dimethylamine, and triethylamine.

A sulfonamide compound represented by general formula (I) can be prepared, for example, by the following process. An isothiazole compound represented by general formula (II):

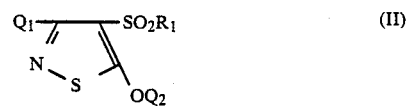

wherein $Q_1$ represents a $-CX_1X_2X_3$ group (wherein each of $X_1$, $X_2$, and $X_3$ independently represents a hydrogen atom or a halogen atom), $Q_2$ represents a $-CH_2CY_1Y_2Y_3$ group (wherein each of $Y_1$, $Y_2$, and $Y_3$ independently represents a halogen atom), $R_1$ represents an $NH_2$ group, an $-NCO$ group, or an

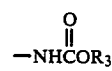

group (wherein $R_3$ is an alkyl group, an alkenyl group, or a phenyl group) or an

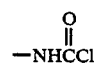

group, is reacted with a pyrimidine compound represented by general formula (III):

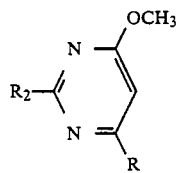 (III)

wherein R is defined as described above, R$_2$ is an NH$_2$ group, an —NCO group, an

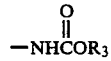

group or an

group, provided that when R$_1$ represents an NH$_2$ group, R$_2$ represents an —NCO group, an

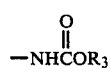

group or an

group, and that when R2 represents an NH2 group, R$_1$ represents an —NCO group, an

group of an

group, and a salt formation treatment is performed, if desired.

It should be noted that the salt formation treatment can be a conventional one.

Process for producing the compounds will be described in more detail as follows.

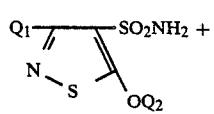 [A]

(II-1)

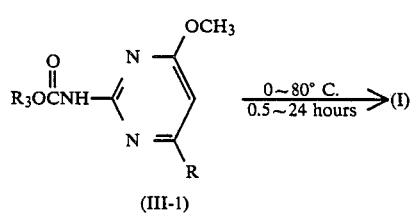

(III-1)

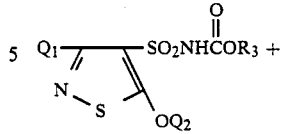 [B]

(II-2)

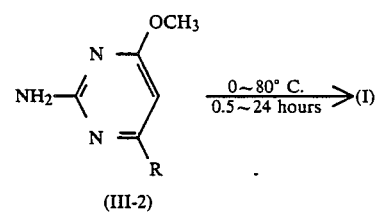

(III-2)

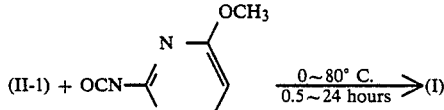 [C]

(III-3)

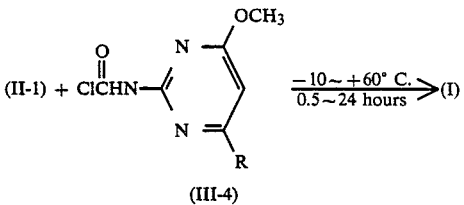 [D]

(III-4)

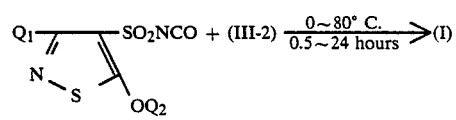 [E]

(II-3)

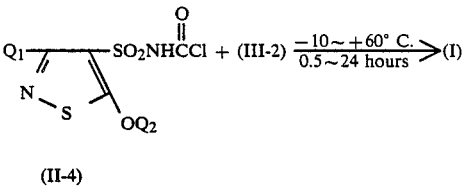 [F]

(II-4)

Other process may be also listed as follows:

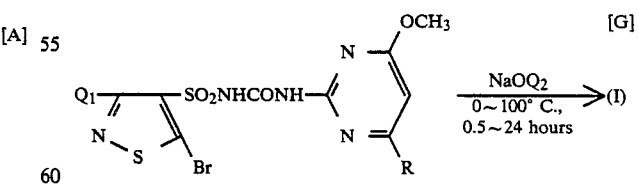 [G]

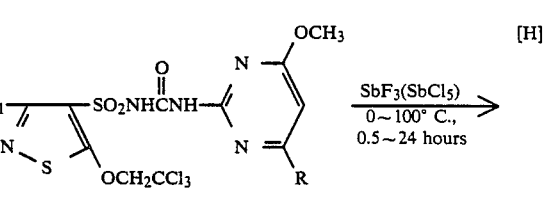 [H]

-continued

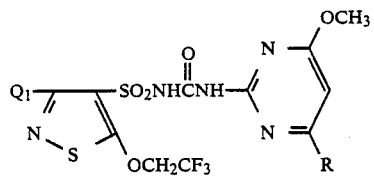

(—OCH₂CF₂Cl or —OCH₂CFCl₂)

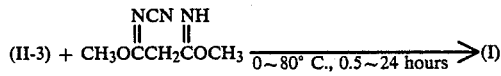  [I]

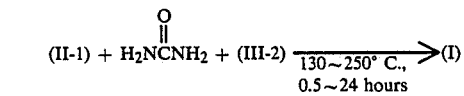  [J]

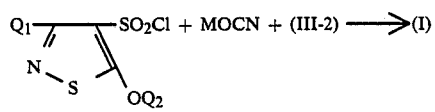  [K]

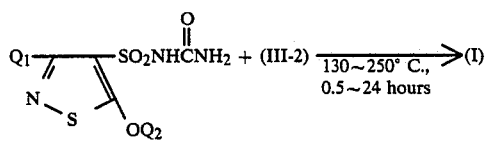  [L]

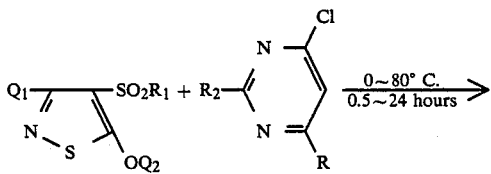  [M]

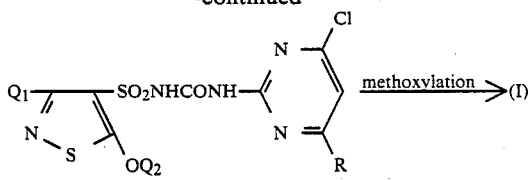

In MOCN used in process [K], M means an alkali metal such as sodium or potassium, an alkali earth metal such as calcium or magnesium, or an amine cation such as triethylamine.

Processes [A] to [M] are practiced in the presence of a solvent, if desired. Examples of the solvent are: aromatic hydrocarbons (e.g., benzene, toluene, xylene, and chlorobenzene); cyclic or acyclic aliphatic hydrocarbons (e.g. chloroform, carbon tetrachloride, methylene chloride, dichloroethane, trichloroethane, hexane, and cyclohexane), ethers (e.g., diethyl ether, dioxane, and tetrahydrofurane); ketones (e.g., acetone, methyl ethyl ketone, and methyl isobutyl ketone); nitriles (e.g., acetonitrile, propionitrile, or acrylonitrile); and aprotic polar solvents (e.g., dimethylsulfoxide and sulfolane); esters (e.g., ethyl acetate).

In reactions by processes [C] to [F], 1,4-diazabicyclo[2.2.2]octane may be added as a catalyst to accelerate the reactions, if desired. In reactions by processes [A] and [B], 1,8-diazabicyclo[5.4.0]-7-undecene may be used to accelerate the reactions, if desired. In reactions by processes [D] and [F], a base such as triethylamine may be added, if desired.

Processes [C] to [F] among processes [A] to [M] are industrially preferable.

A starting material represented by general formula. (II-1) in the reaction above can be shown by processes for producing by, e.g., the following route:

(1) Where starting materials are 5-halogeno-3-methylisothiazoles and a β-iminothiocarbonate compound, the process is shown by route 1 below;

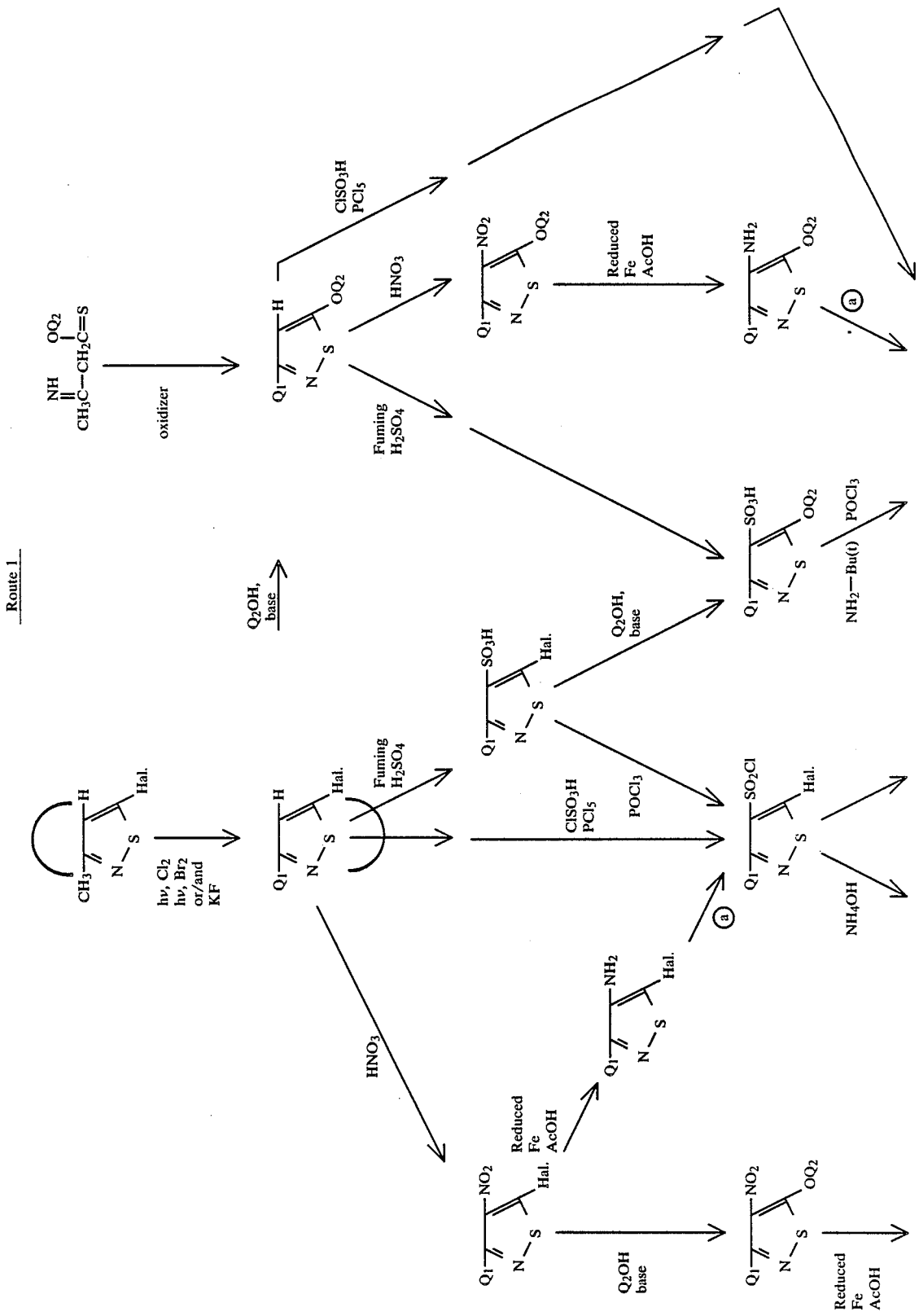

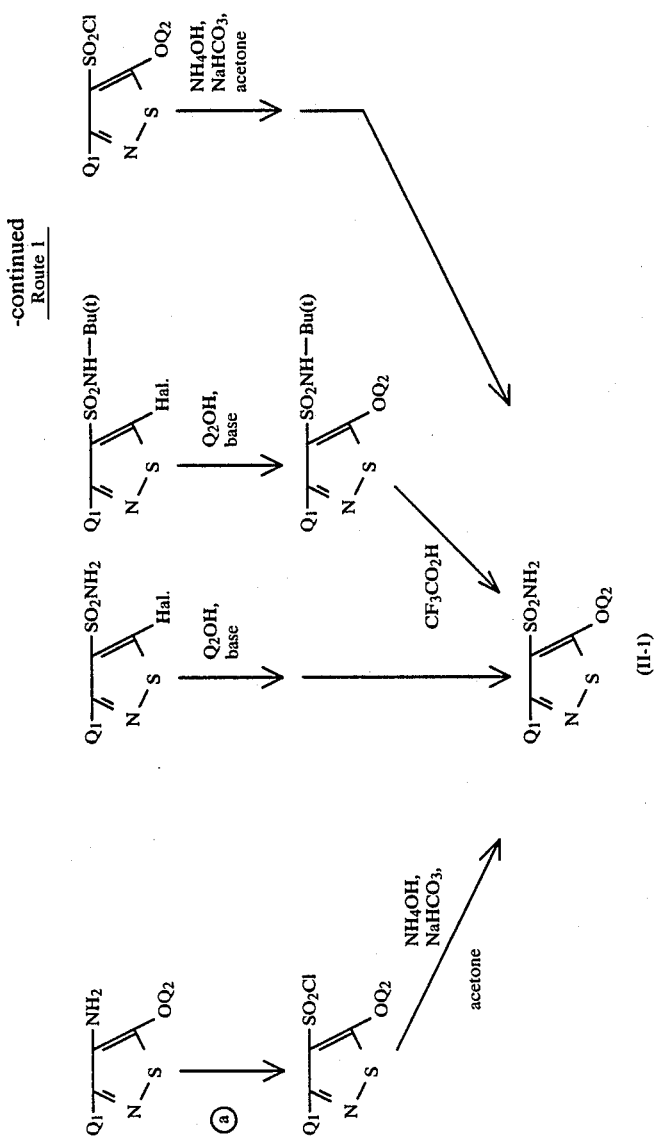

Note:
(1) NaNO$_2$, AcOH, H$_3$PO$_4$, and HCl, and (2) CuCl (or CuCl$_2$), SO$_2$, and AcOH are used in process (a). Bu(t) in NH$_2$-Bu(t) or NH-Bu(t) means a tertiary-butyl group, and AcOH means acetic acid.

(2) Where starting materials are 3-methylisothiazole and 3-bromoisothiazole the process is shown by route 2 below;

Note: ClSO$_3$H or fuming H$_2$SO$_4$ is used in process (b), and fuming nitric acid is used in process (c). n-BuLi means normal butyl lithium.

(3) A process for producing compound represented by general formula (II-1) wherein Q$_1$ represents a CH$_2$F group, a CHF$_2$ group, and a CF$_3$ group is shown by route 3 below;

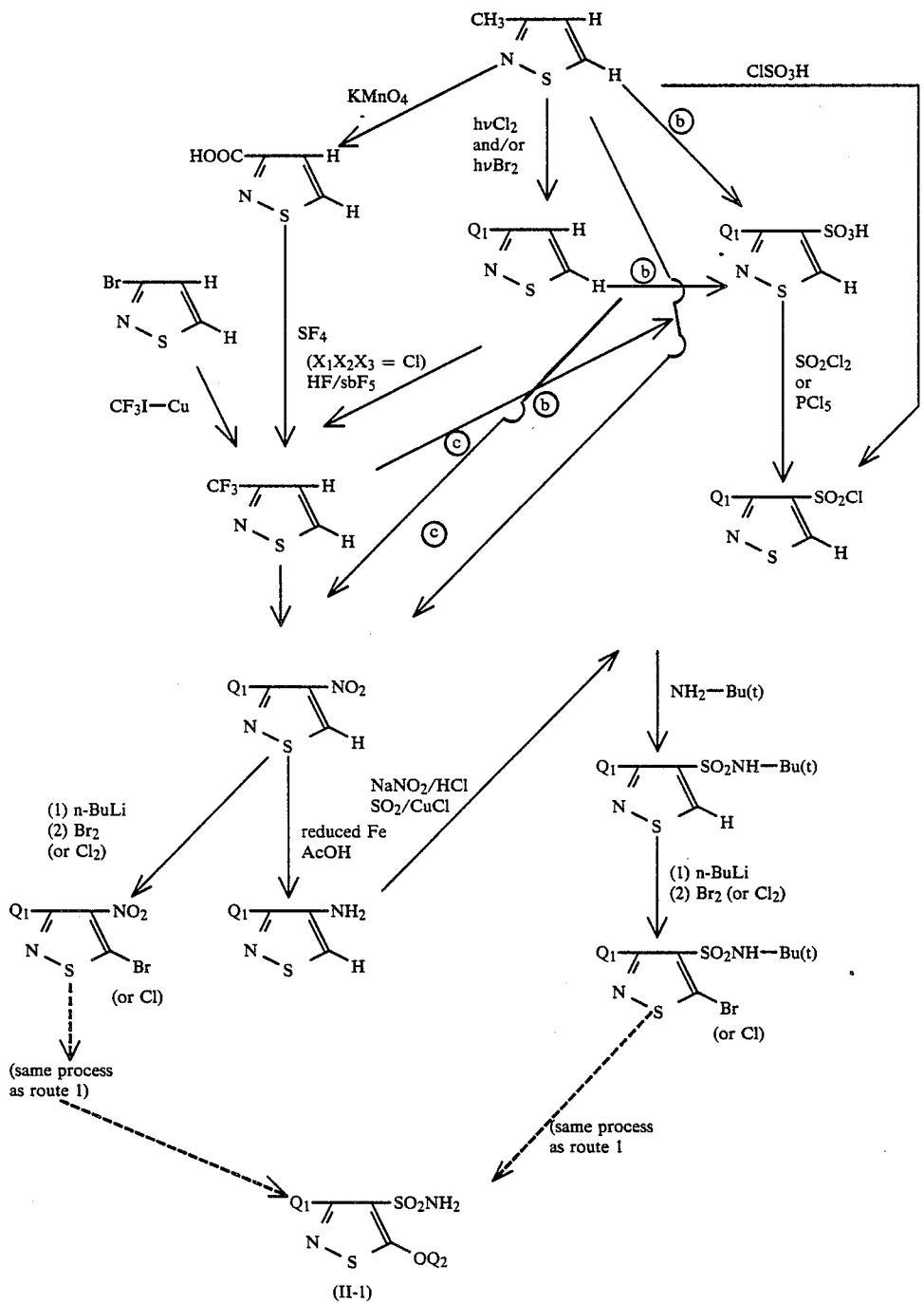

Route 2

Route 3

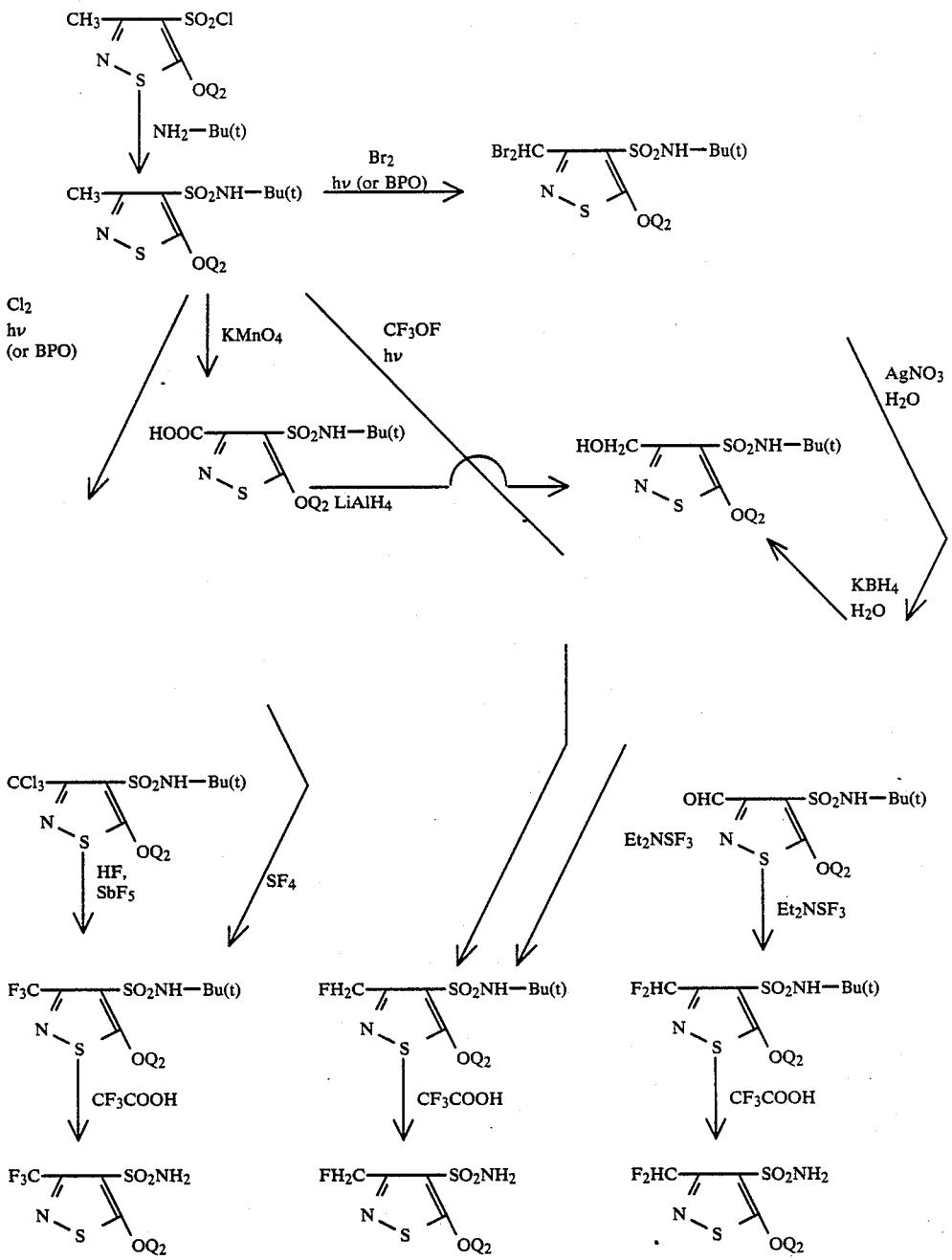
Note: Et₂NSF₃ means diethylamino sulfur trifluoride and BPO means benzoyl peroxide.
A process for producing starting materials represented by general formulas (II-2) to (II-4) can be shown by a process given by route 4 below:
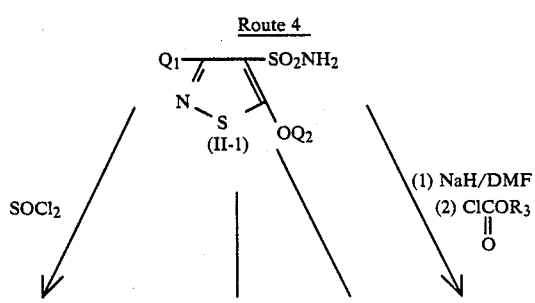

Route 4
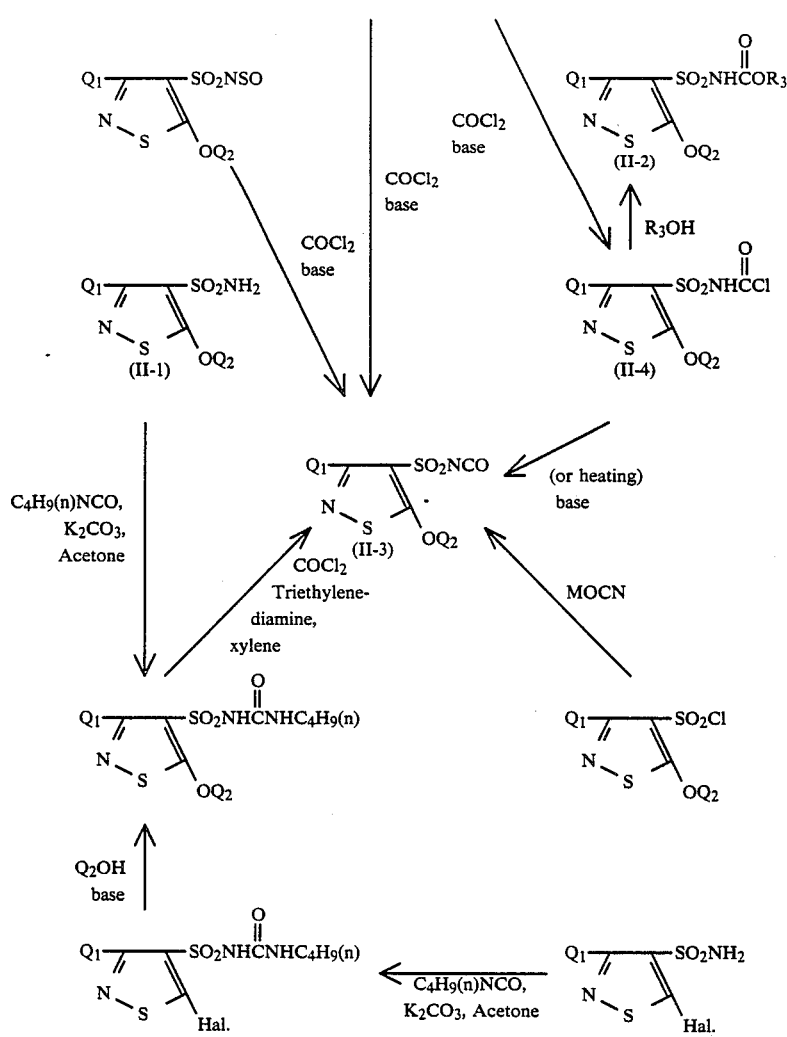
Note: DMF means N,N-dimethylformamide, and MOCN is defined as described in process [K].
Halogen conversion in $Q_2$ is performed as follows:
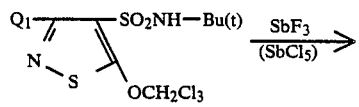
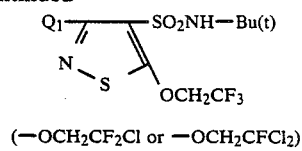
$(-OCH_2CF_2Cl$ or $-OCH_2CFCl_2)$
Starting materials represented by general formulas (III-1), (III-3), and (III-4) in the reactions can be easily derived from the compound represented by general formula (III-2) in the following manner:
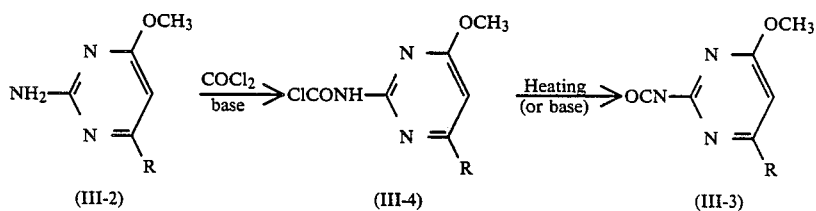

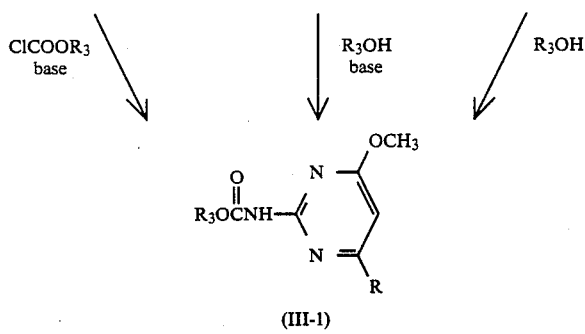

(III-1)

Starting materials used in processes [G] to [M] can be prepared following similar procedures to those of the routes described herein.

Intermediates used in the process for preparing the sulfonamide compounds represented by general formula (I) have been described. Typical examples of the compounds represented by general formula (II) as intermediates are represent as follows:

TABLE 1

$$X_3X_2X_1C\underset{N\diagdown S}{\overset{\diagup\diagdown}{\diagup}}\underset{OCH_2CY_1Y_2Y_3}{\overset{SO_2R_1}{\diagup}} \quad (II)$$

| Inter-mediate No. | General Formula (II) | | | | | | | Property Melting Point (°C.) |
|---|---|---|---|---|---|---|---|---|
| | $X_1$ | $X_2$ | $X_3$ | $R_1$ | $Y_1$ | $Y_2$ | $Y_3$ | |
| 1 | H | H | H | $NH_2$ | F | F | F | 148–149 |
| 2 | " | " | " | NCO | " | " | " | — |
| 3 | " | " | " | O‖NHCCl | " | " | " | — |
| 4 | " | " | " | O‖NHCOC$_6$H$_5$ | " | " | " | 112–114 |
| 5 | " | " | " | $NH_2$ | Cl | Cl | Cl | 140–142 |
| 6 | " | " | " | O‖NHCCl | " | " | " | — |
| 7 | " | " | " | $NH_2$ | *F | F | " | 102–103 |
| 8 | " | " | " | NCO | " | " | " | — |
| 9 | " | " | " | O‖NHCCl | " | " | " | — |
| 10 | F | " | " | $NH_2$ | " | " | F | 70–73 |
| 11 | " | " | " | O‖NHCCl | " | " | " | — |
| 12 | " | F | " | $NH_2$ | " | " | " | 102–104 |
| 13 | " | " | " | O‖NHCCl | " | " | " | — |

Synthetic Examples of compounds according to the present invention will be described below.

SYNTHETIC EXAMPLE 1

(Synthesis of N-[(4,6-dimethoxypyrimidin-2-yl)aminocarbonyl]-3-methyl-5-(2,2,2-trifluoroethoxy)-4-isothiazolesulfonamide (Compound No. 1))

[I] Synthesis of 3-methyl-5-(2,2,2-trifluoroethoxy)-4-isothiazolesulfonamide

Method a (1) 200 g of 30% fuming sulfuric acid were added dropwise in 50.0 g of 5-bromo-3-methylisothiazole over 30 minutes under cooling with water. Then the reacted solution was heated to 170° to 180° C. and subjected to react for 5.5 hours.

After the completion of the reaction, the reaction mixture was poured in 1.5 l of ice and water, and the value of pH thereof was adjusted by calcium carbonate to 7. Resulting calcium sulfate was filtered, and 200 ml of 2N-sulfuric acid were added to the filtrate. The resultant filtrate was heated and filtered again, and water of the filtrate was distilled off to obtain 66.3 g of 5-bromo-3-methyl-4-isothiazolesulfonic acid.

(2) 179.0 g of phosphorus oxychloride were added dropwise into 66.0 g of 5-bromo-3-methyl-4-isothiazolesulfonic acid obtained in the above step (1) over 10 minutes, and the solution was heated to a reflux temperature and reacted for 4 hours.

After the completion of the reaction, the reaction mixture was cooled and poured into 1 l of ice-cold water, and the resulted mixture was stirred and subjected to extract twice with 500 ml of chloroform. The extracted layer was washed with water and dried with anhydrous sodium sulfate. After the chloroform was distilled off and then distilled under reduced pressure to obtain 39.3 g of 5-bromo-3-methyl-4-isothiazolesulfonylchloride having a boiling point of 120° to 125° C./10 mmHg.

(3) A solution prepared by dissolving 39.0 g of 5-bromo-3-methyl-4-isothiazolesulfonylchloride obtained in the above step (2) in 195 ml of 1,4-dioxane was added dropwise to 585 ml of 28% aqueous ammonia over about 1 hour at 5° C. or lower while cooling with ice and water and the mixture was reacted.

After the completion of the reaction, the reaction mixture was poured into 250 ml of brine and extracted with 250 ml of ethyl acetate. The extracted layer was dried, the ethyl acetate was distilled off, and the residue obtained was recrystallized from methanol to obtain 27.5 g of 5-bromo-3-methyl-4-isothiazolesulfonamide having a melting point of 148° to 150° C.

(4) 49.2 g of 2,2,2-trifluoroethanol were stirred with 5.5 g of metal sodium under nitrogen stream for 30 minutes, and 90 ml of 1,4-dioxane were added to the resultant mixture. The resultant mixture was then stirred at 90° to 100° C. for 1.5 hours. 27.0 g of 5-bromo-3-methyl-4-isothiazolesulfonamide obtained in the above step (3) were added to the solution, and the resulted mixture was reacted at a reflux temperature for 3.5 hours.

After the completion of the reaction, the reaction mixture was cooled, and poured into 350 ml of dichloromethane and then 20 ml of concentrated hydrochloric acid and 350 ml of brine were added thereto, thereby separating a layer. The extracted layer was dried, and dichloromethane was distilled off. The resultant viscous material was recrystallized from ethanol to obtain 20.3 g of 3-methyl-5-(2,2,2-trifluoroethoxy)-4-isothiazolesulfonamide having a melting point of 148° to 149° C.

Method b (1) A solution prepared by dissolving 39.6 g of tert-butylamine in 100 ml of dichloromethane was added dropwise in 80 ml of dichloroethane solution containing 15.0 g of 5-bromo-3-methyl-4-isothiazolesulfonylchloride under cooling with ice-cold water over 30 minutes. Then the resulted mixture was reacted at room temperature for 1.5 hours.

After the completion of the reaction, the reaction mixture was poured into 150 ml of cold water, and a separated dichloromethane layer was dried. The dichloromethane was distilled off to obtain 16.1 g of N-tert-butyl-5-bromo-3-methyl-4-isothiazolesulfonamide having a melting point of 118° to 123° C.

(2) 40 ml of 2,2,2-trifluoroethanol were stirred with 1.9 g of metal sodium under nitrogen stream for 15 minutes, and then 5.0 g of N-tert-butyl-5-bromo-3-methyl-4-isothiazolesulfonamide prepared in the above step (1) was added thereto, and reacted at a reflux temperature for 18 hours.

After the completion of the reaction, the reaction mixture was cooled, and poured into a mixture of 64 ml of ethyl acetate and 64 ml of cold water and separated. The separated layer was washed with water and dried. The ethyl acetate was then distilled off to obtain 6.1 g of oily N-tert-butyl-3-methyl-5(2,2,2-trifluoroethoxy)- 4-isothiazolesulfonamide (the resultant oily product is purified by a silica gel column chromatography to obtain a product having a melting point of 87° to 90° C.).

(3) 6.1 g of N-tert-butyl-3-methyl-5-(2,2,2-trifluoroethoxy)-4-isothiazolesulfonamide prepared in the above step (2) and 70 ml of trifluoroacetic acid was reacted while stirring at a reflux temperature for 19 hours.

After the completion of the reaction, the reaction mixture was cooled, and poured into a mixture of 78 ml of ethyl acetate and 78 ml of cold water. The extracted layer was washed with water and an aqueous potassium carbonate solution and dried over. The ethyl acetate was distilled off, and the resulted oily product was crystallized from a solvent mixture of dichloromethane and normal hexane, thereby obtaining 4.2 g of 3-methyl-5-(2,2,2-trifluoroethoxy)-4-isothiazolesulfonamide.

[II] Synthesis of desired Product (Compound No. 1)

Method a

A solution of 5.52 g of 3-methyl-5-(2,2,2-trifluoroethoxy)-4-isothiazolesulfonamide prepared in the step (4) in method a of [I], 8.08 g of triethylamine, and 50 ml of ethyl acetate was added dropwise to a solution obtained by dissolving 3.96 g of phosgene in 46.04 g of ethyl acetate, under cooling at 0° to 3° C. for 30 minutes.

Then 6.2 g of 2-amino-4,6-dimethoxypyrimidine were added to the resulted solution, and after 15 minutes, 4.04 g of triethylamine were added dropwise thereto. The resulted solution was reacted for an hour.

After the completion of the reaction, the reaction mixture was poured into 500 ml of an water containing 20 g of triethylamine, and the value of pH of the resultant solution was adjusted by hydrochloric acid to 3 to precipitate white powder. The filtered precipitate was washed with water and then with an aqueous solution of sodium bicarbonate. The washed precipitate was then purified with ethyl acetate to obtain 4.5 g of compound No. 1 having a melting point of 199° to 200° C.

Method b (1) A solution of 7.75 g of 2-amino-4, 6-dimethoxypyrimidine, 20.2 g of triethylamine, and 77.5 g of ethyl acetate was added dropwise to 49.5 g of an ethyl acetate solution containing 9.9 g of phosgene at 10° to 12° C. for 60 minutes under cooling. The resulted mixture was stirred and reacted at 10° to 15° C. for 16 hours.

After the completion of the reaction, the ethyl acetate and phosgene were distilled off at a temperature lower than 50° C. under reduced pressure, and then the residue was cooled to room temperature.

(2) 200 ml of ethyl acetate and 9.66 g of 3-methyl-5-(2,2,2-trifluoroethoxy)-4-isothiazolesulfonamide were added to the product obtained in the above step (1). 5.3 g of triethylamine were then added dropwise to the solution and the mixture was reacted for an hour.

After the completion of the reaction, following the same procedures as in method a for the Synthetic Example of the desired product, 15.2 g of the product were obtained.

Method c (1) 15.0 g of phosgene were blown in 80 g of chlorobenzene at room temperature, and 250 ml of a chlorobenzene solution containing 15.5 g of 2-amino-4,6-dimethoxypyrimidine were added dropwise to the above solution at 50° to 55° C. while stirred, then reacted at this temperature for an hour.

After the completion of the reaction, a crystal precipitated from the reaction mixture was filtered, and the chlorobenzene was distilled off. After distillation under reduced pressure, 3.0 g of 2-isocyanato-4,6-dimethoxypyrimidine was obtained.

(2) Following the same procedures as in the step (2) of method b of [II] using 2-isocyanato-4,6-dimethoxypyrimidine prepared in the above step (1), a desired product is obtained.

SYNTHETIC EXAMPLE 2

(Synthesis of
N-[(4-methyl-6-methoxypyrimidin-2-yl)aminocarbonyl]-3-methyl-5-(2,2,2-trifluoroethoxy)-4-isothiazolesulonamide (Compound No. 2)

[I] Synthesis of
3-methyl-5-(2,2,2-trifluoroethoxy)-4-isothiazolesulfonamide (1) 0.8 g of metal sodium was dissolved in 30 ml of 2,2,2-trifluoroethanol, and 4.0 g of 5-bromo-3-methyl-4-nitroisothiazole, 0.7 g of cupric oxide, and 16 mg of potassium iodide were added thereto, and the mixture was reacted at a reflux temperature for 30 minutes.

After the completion of the reaction, the reaction mixture was poured into 200 ml of water and extracted with ethyl acetate. The extracted layer was washed with water and dried. The ethyl acetate was distilled off under reduced pressure. The residue was recrystallized from a mixture of normal hexane and ether to give 3.6 g of 3-methyl-4-nitro-5-(2,2,2-trifluoroethoxy)isothiazole having a melting point of 63° to 64° C.

(2) 3.3 g of 3-methyl-4-nitro-5-(2,2,2-trifluoroethoxy)isothiazole prepared in the above step (1) was dissolved in 50 ml of acetic acid, and 3.8 g of reduced iron was added thereto and reacted at a reflux temperature for 5 minutes.

After the completion of the reaction, the reaction mixture was poured into 200 ml of water, and was extracted with ethyl acetate. The extracted layer was washed with aqueous solution of potassium carbonate and then with water. The layer was dried, and the ethyl acetate was distilled off under reduced pressure. The residue was purified by a silica gel column chromatography to give 2.1 g of oily 4-amino-3-methyl-5-(2,2,2-trifluoroethoxy)isothiazole.

(3) 5 ml of acetic acid, 6 ml of 85% phosphoric acid, and 3 ml of concentrated hydrochloric acid was added to 2.1 g of 4-amino-3-methyl-5-(2,2,2-trifluoroethoxy)isothiazole prepared in the above step (2). 2 ml of aqueous solution containing 0.77 g of sodium nitrite was added dropwise to the above mixture at −20° to −10° C. The resulted solution was stirred at −5° C. for 30 minutes and was gradually added dropwise at −10° to −5° C. into 30 ml of an acetic acid solution, which had been saturated with sulfur dioxide and had contained 0.3 g of cuprous chloride. After the completion of dropping, the resulted solution was stirred and reacted at 0° to 5° C. for an hour. After the completion of the reaction, the reaction mixture was poured into ice-cold water, and was extracted with dichloromethane, and the extracted layer was sufficiently washed with water and dried. The solvent was subjected to distillation under reduced pressure to give 1.2 g of oily 3-methyl-5-(2,2,2-trifluoroethoxy)-4-isothiazolesulfonyl chloride.

(4) A solution prepared by dissolving 1.2 g of 3-methyl-5-(2,2,2-trifluoroethoxy)-4-isothiazolesulfonyl chloride prepared by the above step (3) in 10 ml of tetrahydrofuran was added to 12 ml of 28% aqueous ammonia under cooling in ice. The temperature of the resultant solution was raised to room temperature and stirred and reacted for 3 hours.

After the completion of the reaction, the reaction product was poured in 200 ml of water, and was extracted with ethyl acetate. The extracted layer was washed with water and dried, and the ethyl acetate was distilled off under reduced pressure. The residue was purified by a silica gel column chromatography to prepare 0.66 g of 3-methyl-5-(2,2,2-trifluoroethoxy)-4-isothiazolesulfonamide having a melting point of 149° to 150° C.

[II] Synthesis of desired Product (Compound No. 2)

233 mg of 3-methyl-5-(2,2,2-trifluoroethoxy)-4-isothiazolesulfonamide was dissolved in 20 ml of acetonitrile. 88 mg of triethylamine was added to the above solution, and 230 mg of phenyl N-(4-methyl-6-methoxypyrimidin-2-yl)carbamate was added thereto. Subsequently, 20 mg of 1,8-diazabicyclo[5.4.0]-7-undecene was added thereto, and stirred to react at room temperature for 2 hours.

After the completion of the reaction, the reaction mixture was poured into 100 ml of water, and concentrated hydrochloric acid was added dropwise to the resulted solution to render the solution acidic (pH 3), thereby precipitating a white crystal. The crystal was filtered and dried under reduced pressure to give 165 mg of the desired product having a melting point of 159° to 161° C.

SYNTHETIC EXAMPLE 3

(Synthesis of N-(4,6-dimethoxypyrimidin-2-yl-aminocarbonyl)-3-methyl-5-(2,2,2-trichloroethoxy)-4-isothiazolesulfonamide (Compound No. 3))

[I] Synthesis of 3-methyl-5-(2,2,2-trichloroethoxy)-4-isothiazolesulfonamide (1) A mixture of 8.9 g of 5-bromo-3-methyl-4-nitroisothiazole, 12 g of 2,2,2-trichloroethanol, and 100 ml of anhydrous tetrahydrofuran was cooled with ice-cold water, and 3.2 g of 60% sodium hydride were gradually added thereto. The resultant solution was stirred to react at 0° C. for 30 minutes.

After the completion of the reaction, the reaction mixture was poured into 300 ml of water, and was extracted with ethyl acetate. The extracted layer was washed with water and dried. The ethyl acetate was distilled off under reduced pressure. The resultant residue was purified by a silica gel column chromatography to give 8.7 g of 3-methyl-4-nitro-5-(2,2,2-trichloroethoxy)isothiazole having a melting point of 60° to 61° C.

(2) 8.7 g of 3-methyl-4-nitro-5-(2,2,2-trichloroethoxy)isothiazole prepared in the above step (1) were dissolved in 200 ml of acetic acid. The resultant solution was heated to 70° C., and 8.3 g of reduced iron were gradually added thereto. The solution was allowed to cool and stirred to react for 2.25 hours.

After the completion of the reaction, the reaction mixture was poured into 400 ml of water, and was extracted with ethyl acetate. The extracted layer was washed with an aqueous solution of potassium carbonate and then with water. The washed layer was dried, and the ethyl acetate was distilled off under reduced pressure. The residue was refined by a silica gel column chromatography to give 3.9 g of 4-amino-3-methyl-5-(2,2,2-trichloroethoxy)isothiazole having a melting point of 58° to 60° C.

(3) 8.3 ml of acetic acid, 10.9 ml of 85% phosphoric acid, and 5.7 ml of concentrated hydrochloric acid were added to 3.6 g of 4-amino-3-methyl-5-(2,2,2-trichloroethoxy)isothiazole prepared in the above step (2). 3 ml of an aqueous solution containing 1.03 g of sodium nitrite was added dropwise therein at −10° C. The resulted solution was stirred at 0° C. for 2 hours and was gradually added dropwise at −10° to −5° C. into 53 ml of an acetic acid solution which had been saturated with sulfur dioxide and had contained 0.41 g of cuprous chloride. After the completion of dropping, the resulted solution was stirred and reacted at 0° to 5° C. for one hour and then at room temperature for 30 minutes.

After the completion of the reaction, the reaction product was poured into ice-cold water and was extracted with ethyl acetate. The extracted layer was sufficiently washed with water and dried. After dried, the ethyl acetate was distilled off. The residue obtained was purified by a silica gel column chromatography to give 2.3 g of 3-methyl-5-(2,2,2-trichloroethoxy)-4-isothiazolesulfonyl chloride having a melting point of 71° to 74° C.

(4) 2.2 g of 3-methyl-5-(2,2,2-trichloroethoxy)-4-isothiazolesulfonyl chloride prepared in the above step (3) were dissolved in 50 ml of acetone, and 0.54 g of sodium bicarbonate was added thereto. The resultant mixture was cooled to −30° to −40° C, and 1 ml of 28% aqueous ammonia was added thereto. The temperature of the resultant solution was gradually raised to room temperature and stirred and reacted for 1.5 hours.

After the completion of the reaction, the reaction mixture was poured into 200 ml of water, and was extracted with ethyl acetate. The extracted layer was washed with water and dried. The ethyl acetate was distilled off therefrom under reduced pressure 10 ml of a solvent mixture of ether/n-hexane (1/1) were added to the residue obtained to crystallize 1.3 g of 3-methyl-5-(2,2,2-trichloroethoxy)-4-isothiazolesulfonamide having a melting point of 140° to 142° C.

[II] Synthesis of desired Product (Compound No. 3)

200 mg of 3-methyl-5-(2,2,2-trichloroethoxy)-4-isothiazolesulfonamide prepared in the step (4) of Synthetic Example 3 [I] and 177 mg of phenyl N-(4,6-dimethoxypyrimidin-2-yl) carbamate were dissolved in 20 ml of acetonitrile, and 103 mg of 1,8-diazabicyclo [5.4.0]-7-undecene were added thereto, and was stirred and reacted for 15 hours.

After the completion of the reaction, the reaction mixture was poured into 100 ml of water, and concentrated hydrochloric acid was added dropwise to render them acidic, so that a white crystal was precipitated. The crystal was filtered and dried under reduced pressure to give 270 mg of the desired product having a melting point of 176° to 180° C.

Synthetic Example 4
(Synthesis of N-[(4,6-dimethoxypyrimidin-2-yl)aminocarbonyl]-3-difluoromethyl-5-(2,2,2-trifluoroethoxy)-4-isothiazolesulfonamide (Compound No. 8))

[I] Synthesis of 3-difluoromethyl-5-(2,2,2-trifluoroethoxy)-4-isothiazolesulfonamide (1) 9.1 g of tert-butylamine were added at room temperature to 10 ml of a methylene chloride solution containing 3.7 g of 3-methyl-5-(2,2,2-trifluoroethoxy)-4-isothiazolesulfonyl chloride prepared following the same procedures as in the step (3) of Synthetic Example 2 [I], and was reacted at a reflux temperature for 30 minutes.

After the completion of the reaction, the reaction mixture was poured into 200 ml of water, and was extracted with ethyl acetate. The extracted layer was washed with water and dried, and the solvent was distilled off under reduced pressure. The residue obtained was purified by a silica gel column chromatography to give 2.2 g of N-tert-butyl-3-methyl-5-(2,2,2-trifluoroethoxy)-4-isothiazolesulfonamide having a melting point of 87° to 90° C.

(2) 1.06 g of N-tert-butyl-3-methyl-5-(2,2,2-trifluoroethoxy)-4-isothiazolesulfonamide prepared in the above step (1) of Synthesis Example 4, 1.14 g of N-bromosuccineimide and 50 mg of benzoyl peroxide were added to 50 ml of a mixture of anhydrous carbon tetrachloride and anhydrous benzene (the ratio thereof was 9:1), and the resultant solution was reacted under light irradiation at a reflux temperature for 23 hours.

After the completion of the reaction, the reaction product was poured into 200 ml of water, and was extracted with ethyl acetate. The extracted layer was washed with an aqueous solution of potassium carbonate and was then dried. The solvent was distilled off under reduced pressure. The residue obtained was purified by a silica gel column chromatography to give 0.5 g of N-tert-butyl-3-dibromomethyl-5-(2,2,2-trifluoroethoxy)-4-isothiazolesulfonamide having a melting point of 135° to 138° C.

(3) 6 ml of an ethanol solution containing 1.55 g of N-tert-butyl-3-dibromomethyl-5-(2,2,2-trifluoroethoxy)-4-isothiazolesulfonamide prepared in the above step (2) of Example 4 were mixed with 10 ml of an aqueous solution containing 0.6 g of silver nitrate. The resulted solution was reacted at a reflux temperature for 20 minutes. Another 0.6 g of sliver nitrate was further added thereto, and was then reacted at the reflux temperature for an hour.

After the completion of the reaction, the reaction product was poured into 300 ml of water, and was extracted with ethyl acetate. The extracted layer was dried and the solvent was distilled off under reduced pressure. The residue obtained was purified by a silica gel column chromatography to give 1.2 g of oily N-tert-butyl-3-formyl-5-(2,2,2-trifluoroethoxy)-4-isothiazolesulfonamide.

(4) 1.1 g of N-tert-butyl-3-formyl-5-(2,2,2-trifluoroethoxy)-4-isothiazolesulfonamide prepared in the above step (3) of Example 4 was dissolved in 10 ml of dichloromethane, and 1.5 ml of diethylamino sulfur trifluoride were added thereto at −70° C. The resulted mixture was gradually raised to room temperature and was stirred and reacted for 3 hours.

After the completion of the reaction, the reaction mixture was poured into 200 ml of water, and was extracted with ethyl acetate. The extracted layer was dried, and the solvent was distilled off. The residue obtained was purified by a silica gel column chromatography to give 0.7 g of N-tert-butyl-3-difluoromethyl-5-(2,2,2-trifluoroethoxy)-4-isothiazolesulfonamide having a melting point of 105° to 106° C.

(5) 8 ml of trifluoroacetic acid were added to 0.7 g of N-tert-butyl-3-difluoromethyl-5-(2,2,2-trifluoroethoxy)-4-isothiazolesulfonamide prepared in the step (4) of Example 4, and was reacted at a reflux temperature for 2 hours.

After the completion of the reaction, the reaction mixture was poured into 200 ml of water, and was extracted by ethyl acetate. The extracted layer was dried, and the solvent was distilled off under reduced pressure. The residue obtained was treated with an ether/hexane mixture to give 0.13 g of 3-difluoromethyl-5-(2,2,2-trifluoroethoxy)-4-isothiazolesulfonamide having a melting point of 102° to 104° C.

[II] Synthesis of desired Product (Compound No. 8)

Following the same procedures as in [II] of Synthetic Example 3 and using 0.08 g of 3-difluoromethyl-5-(2,2,2-trifluoroethoxy)-4-isothiazolesulfonamide obtained by the step (5) of [I] of Synthetic Example 4, 0.11 g of the desired product having a melting point of 200° to 202° C. was obtained.

SYNTHETIC EXAMPLE 5

(Synthesis of N-[(4,6-dimethoxypyrimidin-2-yl)aminocarbonyl]-3-fluoromethyl-5-(2, (Compound No. 7))

[I] Synthesis of 3-fluoromethyl-5-(2,2,2-trifluoroethoxy)-4-isothiazolesulfonamide (1) 20 ml of a methanol solution containing 1.0 g of N-tert-butyl-3-formyl-5-(2,2,2-trifluoroethoxy)-4-isothiazolesulfonamide were added at 10°–15° C. to an aqueous solution of methanol/0.2N-sodium hydroxide (8 ml/2 ml) containing 72 mg of potassium borohydride, and reacted while stirring at room temperature for 15 hours.

After the completion of the reaction, the reaction product was poured into 200 ml of water, and was extracted with ethyl acetate. The extracted layer was dried, and the solvent was distilled off under reduced pressure. The residue obtained was purified by a silica gel column chromatography to give 0.54 g of N-tert-butyl-3-hydroxymethyl-5-(2,2,2-trifluoroethoxy)-4-isothiazolesulfonamide having a melting point of 113° to 116° C.

(2) 0.51 g of N-tert-butyl-3-hydroxymethyl-5-(2,2,2-trifluoroethoxy)-4-isothiazolesulfonamide prepared in the step (1) of Synthetic Example 5 was dissolved in 20 ml of methylene chloride, and 2 ml of a methylene chloride solution containing 0.47 g of diethylamino sulfur trifluoride were added thereto at −70° C. The resulted solution was gradually raised to room temperature and reacted for 15 hours while stirring.

After the completion of the reaction, the reaction product was poured into 300 ml of water, and was extracted with ethyl acetate. The extracted layer was dried, and the solvent was distilled off under reduced pressure. The residue obtained was purified by a silica gel column chromatography to give 0.44 g of an oily N-tert-butyl-3-fluoromethyl-5-(2,2,2-trifluoroethoxy)-4-isothiazolesulfonamide.

(3) 15 ml of trifluoroacetatic acid was added to 0.44 g of N-tert-butyl-3-fluoromethyl-5-(2,2,2-trifluoroethoxy)-4-isothiazolesulfonamide prepared in the step (2) of Synthetic Example 5, and was reacted while stirring at room temperature for 15 hours.

After the completion of the reaction, the reaction product was poured into 200 ml of water, and was extracted with ethyl acetate. The extracted layer was dried, and the solvent was distilled off under reduced pressure. The residue obtained was purified by a silica gel column chromatography to give 0.30 g of 3-fluoromethyl-5-(2,2,2-trifluoroethoxy)-4-isothiazolesulfonamide having a melting point of 70° to 73° C.

[II] Synthesis of desired Product (Compound No. 7)

Following the same procedures as in [II] of Synthetic Example 3 and using 0.105 g of 3-fluoromethyl-5-(2,2,2-trifluoroethoxy)-4-isothiazolesulfonamide prepared in the step (3) of [I] of Synthetic Example 5, 0.138 g of the desired product having a melting point of 199° to 201° C. was prepared.

Examples of compounds of the invention represented by general formula (I) are summarized in Table 2 below.

TABLE 2

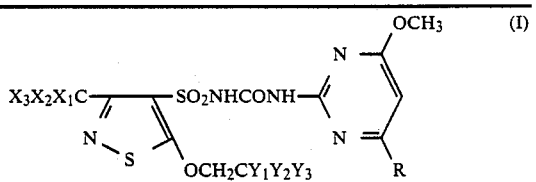

| Compound No. | $X_1$ | $X_2$ | $X_3$ | R | $Y_1$ | $Y_2$ | $Y_3$ | Property Melting Point (°C.) |
|---|---|---|---|---|---|---|---|---|
| 1 | H | H | H | OCH$_3$ | F | F | F | 199–200 |
| 2 | " | " | " | CH$_3$ | " | " | " | 159–161 |
| 3 | " | " | " | OCH$_3$ | Cl | Cl | Cl | 176–180 |
| 4 | " | " | " | CH$_3$ | " | " | " | 179–181 |
| 5 | " | " | " | OCH$_3$ | F | F | " | 182–183 |
| 6 | " | " | " | CH$_3$ | " | " | " | 170–171 |
| 7 | F | " | " | OCH$_3$ | " | " | F | 199–201 |
| 8 | " | F | " | " | " | " | " | 200–202 |

Salts of sulfonamide compounds represented by general formula (I) are as follows:

Compound No. 9

Monomethylamine salt of N-[(4,6-dimethyoxypyrimidin-2-yl)aminocarbonyl]-3-methyl-5-(2,2,2-trichloroethoxy)-4-isothiazolesulfonamide; its melting point is 165° to 7° C.

Compound No. 10

Monomethylamine salt of N-[(4,6-dimethoxypyrimidin-2-yl)aminocarbonyl]-3-methyl-5-(2-chloro-2,2-difluoroethoxy)-4isothiazolesulfonamide; its melting point is 169° to 171° C.

Compound No. 11

Calcium salt of N-[(4,6-dimethoxypyrimidin-2-yl)aminocarbonyl]-3-methyl-5-(2,2,2-trifluoroethoxy)-4-isothiazolesulfonamide; its melting point is 229° to 232° C.

The sulfonamide compounds and their salts exhibit an excellent herbicidal effect as shown later when they are used as active ingredients of herbicidal compositions. In particular, noxious weeds growing in paddy fields can be selectively killed at a low dosage without causing phytotoxicity of rice plants. Examples of the noxious weeds are: *cyperaceae* such as japanese bulrush (*Scirpus hotarui*), *Cyperus serotinus*, small-flower umbrellaplant (*Cyperus difformis*), slender spikerush (*Eleocharis acicularis*), and *Eleocharis kuroguwai*; *alismataceae* such as japanese ribbon wapato (*Sagittaria pygmaea*), arrowhead (*Sagittaria trifolia*), and *Alisma canaliculatum*; *pontederiaceae* such as monochoria (*Monochoria vaginalis*); *scrophulariaceae* such as false pimpernel (*Lindernia pyxidaria*); *lythraceae* such as toothcup (*Rotara indica*); and *gramineae* such as barnyard-grass (*Echinochloa crusgalli*). Even if noxious weeds are considerably grown, they can be killed by the compounds of the present invention. Therefore, the compounds can be conveniently used as the herbicidal compositions for paddy fields. The compounds of the present invention also exhibit an excellent herbicidal effect for noxious upland weeds.

Herbicides according to the present invention will find an application such as upland farms and many other applications such as agricultural fields, e.g., orchards and mulberry fields and nonagricultural fields, e.g., forests, farm roads, playgrounds, and factory sites. The herbicidal composition of the present invention can be applied by soil treatment or foliar treatment, if desired.

When a herbicidal composition of the present invention is applied, the herbicidal compound of the present invention is usually formulated into various forms such as granules, wettable powder, emulsifiable concentrate, liquid formulation, or water-soluble powder by optionally incorporating conventional agriculturally acceptable adjuvants, e.g., a carrier in a normal application, and a diluent, solvent, emulsifier, spreader or surfactant, if desired.

Examples of the agriculturally acceptable adjuvant are: solid carriers such as diatomaceous earth, hydrated lime, calcium carbonate, talc, white carbon, kaoline, bentonite, jeaklite, clay, and starch; solvents such as water, toluene, xylene, solvent naphtha, dioxane, acetone, isophorone, methyl isobutyl ketone, chlorobenzene, cyclohexane, dimethylsulfoxide, dimethylformamide, N-methyl-2-pyrrolidone, and alcohol; and spreaders and surfactants such as sodium alkyl sulfate, sodium alkylbenzene sulfonate, sodium lignin sulfonate, polyoxyethylene alkylaryl ether sulfate, polyoxyethylene glycol alkyl ether, polyoxyethylene lauryl ether, polyoxyethylene alkylaryl ether, an ester of polyoxyethylene aliphatic acid, an ester of polyoxyethylene sorbitan aliphatic acid. However, the adjuvants are not limited to the ones described above.

A suitable mixing ratio [(a):(b)] of the active ingredient (a) to the adjvant(s) (b) ranges from 0.02:99.98 to 90:10, and preferably 0.03:99.97 to 60:40. An optimum amount of the active ingredient applied cannot be unequivocally defined because it varies according to various factors such as the climate condition, the weather condition, the soil condition, the form of the chemicals, the type of weeds to be controlled, or the time of application, but the amount of the active ingredient is usually from 0.05 to 50 g per are, preferably 0.1 to 30 g per are. The herbicidal composition of the present invention can be mixed or used together with other agricultural chemicals, fertilizers, soil, or safteners. Such a conjoint use brings about a more excellent effect or action. Examples of other herbicides which can be mixed with the herbicidal composition of the present invention are listed below:

2,4-dichlorophenyl-3'-methoxy-4'-nitrophenylether, 2,4-dichlorophenyl-3'-methoxycarbonyl-4'-nitrophenylether, 2-chloro-2',6'-diethyl-N-(butoxymethyl)acetanilide, 2-chloro-2',6'-diethyl-N-(propoxyethyl)acetanilide, S-[(2-methyl-1-piperidyl)-carbonylmethyl]-O,O-di-n-propylthiophosphate, S-(4-chlorobenzyl)-N,N-diethylthiocarbamate, S-ethyl-hexahydro-1H-azepin-1-carbothioate, S-(1-methyl-1-phenethyl)piperidine-1-carbothioate, S-benzyl-N-ethyl-N-(1,2-dimethylpropyl)thiocarbamate, 2-naphthyl-N-methyl-N-(2-methoxy-6-pyridyl)thiocarbamate, O-(meta-tert-butylphenyl)-N-methyl-N-(6-methoxypyridin-2-yl)-thiocarbamate, 5-tert-butyl-3-(2,4-dichloro-5-isopropoxydiphenyl)-1,3,4-oxadiazolin-2-one, 2-benzthiazol-2-yloxyaceto-N-methylanilide, 4-(2,4-dichlorobenzoyl)-1,3-dimethyl-5-phenacyloxypyrazole, 4-(2,4-dichlorobenzoyl)-1,3-dimethylpyrazol-5-yl-p-toluene sulfonate, 4-(2,4-dichloro-3-methylbenzoyl)-1,3-dimethyl-5-(4-methyl phenacyloxy)pyrazole, and 3,7-dichloro-8-quinolinecarboxylic acid.

When the herbicidal composition of the present invention is used together or mixed with other herbicidal compounds, an optimum amount of the active ingredient applied cannot be unequivocally defined because it varies according to various factors such as the climate condition, the weather condition, the soil condition, the form of the chemicals, the type of weeds to be controlled, or the time of application, but the amount of a herbicidal compound to be used or mixed with 1 part by weight of the isothiazole compound or a salt thereof is 0.1 to 200 parts by weight and, preferably 0.5 to 100 parts by weight, and a rate of application of a total active ingredient is 1 to 100 g per are and, preferably 2 to 50 g per are.

The time of application of the active ingredient is normally a period between time prior to sprout of weeds and the 3- or 4-leaf stage thereof. In the case of transplantation of rice plants in paddy fields, the time of application is a period between the time prior to transplantation to about 20 days after transplantation. The active ingredient is mixed with various adjuvants according to normal agricultural chemical preparation methods. For example, the herbicidal compound of the present invention is usually formulated into forms such as an emulsifying concentrate, wettable powder, and granules. The compounds containing active ingredients may be mixed or formulated together. Alternatively, active ingredients may be separately formulated and then mixed together.

Test examples of herbicides of the present invention will be described below.

TEST EXAMPLE 1

Each 1/10,000 are pot was charged with soil of paddy fields, and seeds of japanese bulrush and germinated tubers of japanese ribbon wapato were sown and planted and each pot was kept in a wet state. After japanese bulrush reached 0.5- to 1-leaf stage, water was filled to a level of about 3 cm. A wettable powder of a predetermined compound was diluted with water, and a predetermined amount of the herbicide was dropped with a pipet. 20 to 21 days after the application, the growing state was visually observed and weed control, i.e., the degree of growth was evaluated on a scale of 5 grades in which 5 indicates that the plant was completely killed and 1 indicates one the same as untreated check, as shown in Table 3 below.

TEST EXAMPLE 2

Each 1/10,000 are pot was charged with soil of paddy fields, and the soil was saturated with water. Seeds of barnyard-grass were sown and slightly covered with the soil. The seeds sprouted in an upland condition. When coleoptiles appeared, each pot was filled with water to a level of 3 cm. A wettable powder having a predetermined compound was diluted with water, and a predetermined amount of the herbicide was dropped with a pipet. 16 to 22 days after the application of the herbicide, the growing state was visually observed and was evaluated on the scale of 5 grades as in Test Example 1, and results are summarized in Table 3 below.

TEST EXAMPLE 3

Each 1/10,000 are pot was charged with soil of paddy fields and filled with water to a predetermined level. The soil was puddled. The next day after puddling, 2.5-leaf stage rice plants (variety: "Nihon-bare") were respectively transplanted one per pot. Four days after the transplantation, a wettable powder of a predetermined compound was diluted with water, and a predetermined amount of the herbicide was dropped with a pipet. 21 to 35 days after the application, the growing state was visually checked and was evaluated on the scale of 5 grades as in Test Example 1. The results are summarized in Table 3 below.

TABLE 3

| Compound No. of Present Invention | Active Ingredient (g/a) | Degree of Growth Inhibition | | | |
|---|---|---|---|---|---|
| | | Japanese bulrush | Japanese ribbon wapato | Barnyard-grass | Rice plant |
| 1 | 0.6 | 5 | 5 | 5 | 1 |
| | 0.3 | " | " | " | " |
| | 0.15 | " | " | 4–5 | " |
| 2 | 0.6 | " | " | 5 | " |
| | 0.3 | " | " | " | " |
| | 0.15 | " | " | " | " |
| 3 | 1.2 | " | " | " | " |
| | 0.6 | " | " | " | " |
| | 0.3 | 4 | " | 4–5 | " |
| 4 | 2.5 | 5 | 5–4 | 5 | " |
| | 1.2 | " | 4 | " | " |
| | 0.6 | 5–4 | " | " | " |
| 5 | 0.6 | 5 | 5 | " | " |
| | 0.3 | " | " | " | " |
| | 0.15 | " | " | " | " |
| 6 | 0.6 | " | " | " | " |
| | 0.3 | " | " | " | " |
| | 0.15 | " | " | " | " |
| 7 | 0.6 | " | 5–4 | 3 | 2 |
| | 0.3 | " | " | " | 1 |
| 8 | 0.6 | " | 5 | 4 | " |
| | 0.3 | " | " | 3 | " |
| 9 | 0.6 | " | " | 5–4 | " |
| | 0.3 | " | 4–5 | 4 | " |
| 10 | 0.6 | " | 5 | 5 | " |
| | 0.3 | " | " | 5–4 | " |

TEST EXAMPLE 4

Each 1/1,700 are plastic case was charged with soil of paddy fields and was maintained in a paddy condition, and seeds of barnyard-grass, japanese bulrush, and monochoria were sown, and germinated tubers of *Eleocharis kuroguwai* and arrowhead were planted therein: Each plastic case was placed outdoors. When barnyard-grass reached the 2-leaf stage, granules of the chemicals were applied at predetermined amounts.

One month after the application of the granules, the growing state was visually observed and evaluated as in Test Example 1. The results are summarized in Table 4.

TABLE 4

| Compound (Active Ingredient, g/a) | Degree of Growth Inhibition | | | | |
|---|---|---|---|---|---|
| | Barnyard-grass | Japanese bulrush | Monochoria | *Eleocharis kuroguwai* | Arrow-head |
| Compound No. 1 (0.24) | 4 | 5 | 5–4* | 5 | 5 |
| Compound No. 1 (0.24) + Compound A (2.7) | 5 | 5 | 5 | 5 | 5 |
| Compound No. 1 (0.24) + Compound B (12) | 5 | 5 | 5 | 5 | 5 |
| Compound No. 1 (0.24) + Compound C (21) | 5 | 5 | 5–4* | 5 | 5 |
| Compound No. 1 (0.24) + Compound D (10.5) | 5–4 | 5 | 5 | 5 | 5 |
| Compound No. 1 (0.24) + Compound E (10.5) | 5 | 5 | 5 | 5 | 5 |
| Compound No. 1 (0.24) + Compound F (6) | 5–4 | 5 | 5–4* | 5 | 5 |

Note:
(1) An asterisk indicates that some seeds of monochoria were partially sprouted 20 days after the application.

(2) Compound A: 3,7-dichloro-8-quinolinecarboxylic acid; Compound B: S-[(2-methyl-1-piperidyl)carbonylmethyl]-O,O-di-n-propyl dithiophosphate; Compound C: S-benzyl-N-ethyl-N-(1,2-dimethylpropyl)thiocarbamate; Compound D: 2-naphthyl-N-methyl-N-(2-methoxy-6-pyridyl)thiocarbamate; Compound E: 2-benzthiazole-2-yloxy acetate-N-methylanilide; and Compound F: 2-chloro-2',6'-diethyl-N-(propoxyethyl)acetanilide.

Other compounds, Compound Nos. 2 to 10, of the present invention can also provide an excellent herbicidal effect by mixing them with other chemicals in the same manner as in Compound No. 1.

TEST EXAMPLE 5

Each outdoor 0.36 m² concrete pot was charged with soil of paddy fields and filled with water to a predetermined level. The soil was puddled. Nine hills (three plants/hill) of 2.5-leaf paddy rice plants (variety "Nihon-bare") were transplanted in each pot, and the water level was kept to be 5 cm. Six days after the transplantation, granules of chemicals were applied at predetermined amounts. The day after the application, water was leached from the bottom at a rate of 3 cm/8 hours/day for 2 days. 55 days after the above treatment, the foliage portions were cut, and the average number of stems of the 9 hills and the average weight of stems and leaves thereof were measured. The measured values were figured in percentage with respect to the non-treated case. Results are shown in Table 5.

TABLE 5

| Compound | Active Ingredient, g/a | Number of Stems (%) | Average Weight of Stems and Leaves (%) |
|---|---|---|---|
| Compound 1 | 0.48 | 94 | 96 |
| Compound 1 + Compound A | 0.48 + 5.4 | 95 | 97 |

Compound A is the same as that in Table 4.

Formulation examples of herbicidal compositions according to the present invention will be described below.

FORMULATION EXAMPLE 1

| | parts by weight |
|---|---|
| (1) Jeeklite | 78 |
| (2) Lavelin S (tradename: manufactured by Daiichi Kogyo Seiyaku Co., Ltd.) | 2 |
| (3) Sorpol 5039 (tradename: manufactured by Toho Chemical Co., Ltd.) | 5 |

-continued

| | parts by weight |
|---|---|
| (4) Carplex (tradename: manufactured by Shionogi & Co., Ltd.) | 15 |

Ingredients (1) to (4) is mixed with compound No. 2 at a weight ratio of 9:1 to prepare a wettable powder.

| | parts by weight |
|---|---|
| (1) Compound No. 1 | 0.08 |
| (2) Sorpol 5146 (tradename: manufactured by Toho Chemical Co., Ltd.) | 6 |
| (3) Noigen EA-112 (tradename: manufactured by Daiich Kogyo Seiyaku Co., Ltd.) | 2 |
| (4) Jeeklite | 25 |
| (5) Bentonite | 66.92 |

Ingredients (1) to (5) are kneaded with a small amount of water and molded into granules, and the granules are dried.

| | parts by weight |
|---|---|
| (1) Compound No. 3 | 0.1 |
| (2) 3,7-dichloro-8-quinolinecarboxylic acid | 1 |
| (3) Calcium lignin sulfonate | 3 |
| (4) Bentonite | 44 |
| (5) Jeeklite | 51.9 |

Ingredients (1) to (5) are mixed, pulverized, and molded to obtain granules.

| | parts by weight |
|---|---|
| (1) Compound No. 5 | 3 |
| (2) 3,7-dichloro-8-quinolinecarboxylic acid | 20 |
| (3) Jeeklite | 52 |
| (4) White carbon | 20 |
| (5) Condensate of sodium naphthalenesulfonate and formaldehyde | 3 |
| (6) Sulfate of polyoxyethylene alkylaryl ether | 2 |

Ingredients (1) to (6) are mixed and pulverized to prepare a wettable powder.

FORMULATION EXAMPLE 5

| [A] | parts by weight |
|---|---|
| (1) Compound No. 1 | 0.08 |
| (2) Bentonite | 40 |
| (3) Jeeklite | 56.92 |
| (4) Calcium lignin sulfonate | 3 |

Ingredients (1) to (4) are mixed, pulverized, and molded to prepare granules [A].

| [B] | parts by weight |
|---|---|
| (1) 3,7-dichloro-8-quinolinecarboxylic acid | 1 |
| (2) Bentonite | 40 |
| (3) Jeeklite | 56 |
| (4) Calcium ligninsulfonate | 3 |

Ingredients (1) to (4) are mixed, pulverized, and molded to prepare granules [B].

Granules [A] and [B] are mixed in a weight ratio of 1:1 to obtain final granules.

FORMULATION EXAMPLE 6

| | parts by weight |
|---|---|
| (1) Water-soluble starch | 75 |
| (2) Sodium ligninsulfonate | 5 |
| (3) Compound No. 9 | 20 |

Ingredients (1) to (3) are mixed to prepare a water-soluble powder.

FORMULATION EXAMPLE 7

| | parts by weight |
|---|---|
| (1) Newlite (tradename: manufactured by Nihon Taika Genryo K.K.) | 97 |
| (2) Discsol W-92 (tradename: Daiichi Kogyo Seiyaku) | 2 |
| (3) Compound No. 8 | 1 |

Ingredients (1) to (3) are mixed and pulverized to prepare dust.

What is claimed is:

1. A sulfonamide compound and a salt thereof, the sulfonamide compound being represented by the following formula:

$$X_3X_2X_1C-\underset{N_{\diagdown S}}{\overset{}{\underset{}{\bigg|}}}-SO_2NHCONH-\underset{OCH_2CY_1Y_2Y_3}{\overset{OCH_3}{\underset{R}{\bigg|}}}$$

wherein each of $X_1$, $X_2$, and $X_3$ independently represents a hydrogen atom or a halogen atom, each of $Y_1$, $Y_2$, and $Y_3$ independently represents a halogen atom, and R represents a methyl group or a methoxy group.

2. A compound and a salt thereof according to claim 1, wherein each of $X_1$, $X_2$, and $X_3$ independently represents a hydrogen atom or a fluorine atom.

3. A compound and a salt thereof according to claim 1, wherein each of $X_1$, $X_2$, and $X_3$ independently rpresents a hydrogen atom.

4. A compound and a salt thereof according to claim 1, wherein each of $Y_1$, $Y_2$, and $Y_3$ independently represents a chlorine atom or a fluorine atom.

5. A compound and a salt thereof according to claim 1, wherein each of $X_1$, $X_2$, and $X_3$ independently represents a hydrogen atom, each of $Y_1$, $Y_2$, and $Y_3$ independently represents a chlorine atom or a fluorine atom.

6. A compound and a salt thereof according to claim 1, wherein the compound is N-[(4,6-dimethoxypyrimidin-2-yl)aminocarbonyl]-3-methyl-5-(2,2,2-trifluoroethoxy)-4-isothiazolesulfonamide.

7. A compound and a salt thereof according to claim 1, wherein the compound is N-[(4,6-dimethoxypyrimidin-2-yl)aminocarbonyl]-3-methyl-5-(2,2,2-trichloroethoxy)-4-isothiazolesulfonamide.

8. A compound and a salt thereof according to claim 1, wherein the compound is N-[(4,6-dimethoxypyrimidin-2-yl)aminocarbonyl]-3-methyl-5-(2-chloro-2,2-difluoroethoxy)-4-isothiazolesulfonamide.

9. A compound and a salt thereof according to claim 1, wherein the compound is N-[(4-methyl-6-methoxypyrimidin-2-yl)aminocarbonyl]-3-methyl-5-(2-chloro-2,2-difluoroethoxy)-4-isothiazolesulfonamide.

10. A herbicidal composition essentially consisting of a herbicidally effective amount of the sulfonamide compound and the salt thereof defined in claim 1 and an agricultural adjuvant.

11. A composition according to claim 10, wherein a mixing ratio of the sulfonamide compound and the salt thereof to the agriculturally acceptable adjuvant is 0.02:99.98 to 90:10.

12. A method for killing weeds, comprising applying to the locus to be protected the herbicidal composition defined in claim 10 at a rate of 0.05 to 50 g/are in paddy rice fields based on the amount of a sulfonamide compound and a salt thereof.

* * * * *